Figure 1:
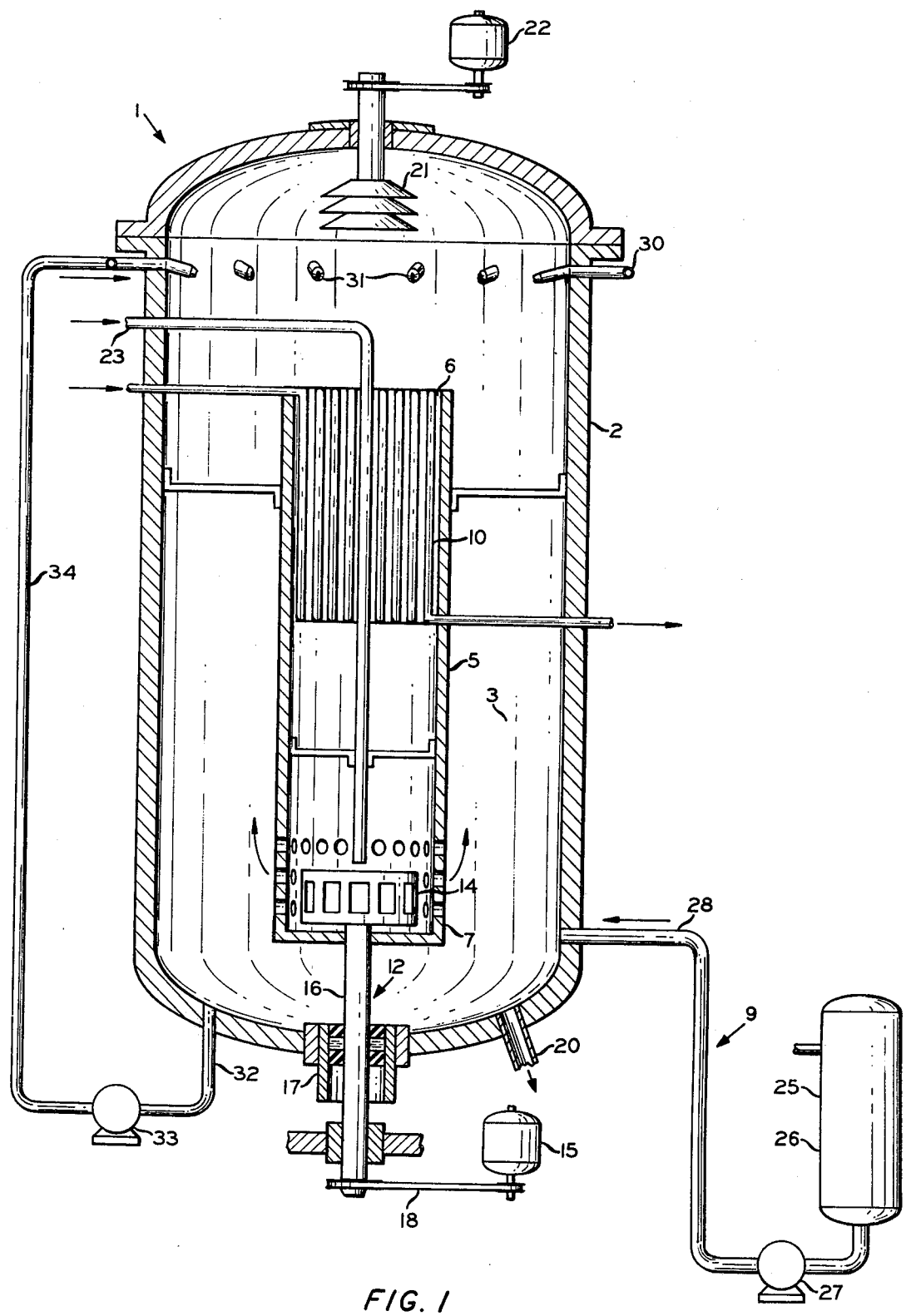

United States Patent
Malick

[11] 3,957,585
[45] May 18, 1976

[54] METHOD FOR CONDUCTING FERMENTATION

[75] Inventor: Emil A. Malick, Bartlesville, Okla.

[73] Assignee: Phillips Petroleum Company, Bartlesville, Okla.

[22] Filed: Jan. 30, 1975

[21] Appl. No.: 545,546

[52] U.S. Cl. ............................... 195/109; 195/142
[51] Int. Cl.² ........................................ C12B 1/14
[58] Field of Search ............................. 195/109, 142

[56] References Cited
UNITED STATES PATENTS

| | | | |
|---|---|---|---|
| 2,200,581 | 5/1940 | Pruss et al. | 195/109 |
| 2,244,902 | 6/1941 | Stich | 195/109 |
| 3,041,181 | 6/1962 | Simonin et al. | 195/109 |
| 3,131,131 | 4/1964 | Wehner | 195/109 |
| 3,201,327 | 8/1965 | Beck | 195/109 |
| 3,625,834 | 12/1971 | Muller | 195/109 |

*Primary Examiner*—Alvin E. Tanenholtz

[57] ABSTRACT

An apparatus for conducting a fermentation process for the production of single cell protein and the like. The apparatus includes a vessel with a reaction zone and has liquid atomizing means opening thereinto for the injection of atomized liquid into the reaction zone to effect intimate contact of the atomized liquid with a gas phase in the reaction zone. Fermentation medium is supplied to the reaction zone and provides a source of carbon and energy for the culturing of a microorganism and preferably before introduction into the reaction zone said medium is saturated with an oxygen-containing gas.

6 Claims, 1 Drawing Figure

METHOD FOR CONDUCTING FERMENTATION

In fermentation processes such as those conducted to produce single cell protein or the like, it is desirable to have high oxygen transfer rates so as to effect high growth rates of the microorganisms. Higher growth rates are desirable as fermentation equipment is costly and higher growth rates make fermentation processes more economical or require smaller equipment to produce the same amount of product. Cellular products high in protein content produced by such fermentation processes are becoming increasingly important because of the current world-wide food shortage and more particularly the protein shortage. Typical fermentation processes include the fermentation of a feedstock employing a suitable microorganism which consumes portions of the feedstock which provides a source of carbon and energy, e.g., methanol or other suitable carbonaceous material as is known. Processes can be either continuous or of a batch type. High oxygen transfer rates have been achieved by conducting the fermentation process as a foam-type process which will effect high surface area contact between the liquid and gas phases and thereby achieve high oxygen transfer rates. To date, many attempts have been made to achieve higher oxygen transfer rates with varied success. Typical fermentation processes are disclosed in U.S. Pat. No. 3,634,194, issued Jan. 11, 1972; U.S. Patent Re. 26,502, issued December 10, 1968; and, U.S. Patent 3,546,071, issued December 8, 1970 but the present invention is not limited to any particular process or materials used in the processes.

The principal objects of the present invention are: to provide an apparatus and method for conducting aerobic fermentation processes having high oxygen transfer rates; to provide such an apparatus which will effect improved and more intimate contact of liquid and oxygen containing gas; to provide such an apparatus which is simple in construction and economical to manufacture and maintain; and to provide such an apparatus and method of fermentation which is well adapted for its intended use.

Other objects and advantages of the present invention will become apparent from the following detailed description taken in connection with the accompanying drawings wherein are set forth by way of illustration and example certain embodiments of this invention.

FIG. 1 is a side elevational sectional view of a fermentation apparatus.

Referring more in detail to the drawings:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate detailed structure.

The reference numeral 1 designates generally a fermentation apparatus comprised of a vessel 2 having a chamber or reaction zone 3. The vessel 2 may be of any suitable structure and preferably has mounted therein a draft tube 5 having opposite ends 6 and 7 and defining a flow path. Means 9 communicate with the reaction zone 3 and are operable to supply feedstock thereto. Feedstock, as used hereafter, preferably is a fluid which is either singularly or in combination a source of carbon and energy (a carbonaceous material), mineral nutrients, (preferably an aqueous mixture thereof) and other substances necessary for the growth of a microorganism. The feedstock preferably is an admixture of the above. Suitable heat exchange means 10 are in heat transfer relation with the vessel 2 for a purpose to be later described.

In the structure illustrated, circulation inducing means 12 are provided and are operable to induce circulation of ferment within the reaction zone 3. Any suitable means 12 can be used and, as shown, said means 12 includes a turbine type pump 14 positioned adjacent the bottom end 7 of the draft tube and is operably connected to power means such as a motor 15 for power operation thereby. Preferably, the turbine 14 induces flow of ferment downwardly through a flow path defined by the draft tube 5 and then upwardly through a flow path defined by the interior of the vessel 2 and the exterior of the draft tube 5. The turbine is mounted on a shaft 16 which is rotatably mounted in a bearing arrangement 17 with the shaft 16 being in driving engagement with the motor 15 by drive means 18.

A conduit 20 is in communication with the reaction zone 3 and is adapted for removing product produced by the fermentation process from the vessel 2. The conduit 20 is positioned to communicate with the reaction zone at any location suitable for removal of product and is not to be limited to the position shown. In the event that the process is a foam-type process, means are provided to separate the foam into a liquid phase and a gas phase. Any suitable type of foam separation can be provided and, as shown, a centrifugal foam separator 21 is mounted in the reaction zone 3 and is operably connected to power means such as a motor 22 for operation thereby. A vent (not shown) is preferably provided for exhaust of gas from an upper portion of the reaction zone 3 and can be a part of the foam separator 21 or a separate vent. The mechanical foam separator 21 can be used in addition to or in place of a chemical defoamer which can be introduced into the reaction zone as required.

Oxygen is supplied to the reaction zone as is required by the particular fermentation process. One means of supplying oxygen is to provide a conduit 23 which has an open end adjacent to the turbine 14 so that the oxygen dispensed through the conduit 23 is mixed with the ferment by action of the turbine 14. The conduit 23 can be used either alone or in connection with additional oxygen supply means 25 which can also be used alone. In this invention, it is to be understood that the term "oxygen" means oxygen alone or in combination with other gases such as in air wherein oxygen can be supplied in any suitable form. Any suitable oxygen supply means 25 can be used and in the illustrated structure same is part of the feedstock supply means 9 and includes a source 26 of feedstock from which feedstock is supplied to the reaction zone. The source of feedstock can be a separate source of various components of the feedstock which can be supplied to the reaction zone 3 before admixture. It is to be noted that the various components of the feedstock can be separately saturated with oxygen or some of the components could be supplied without being saturated with oxygen. As shown, a pump 27 is in communication with the source 26 and is operable to supply feedstock therefrom to the reaction zone 3 by a conduit 28. The pump pressurizes the feedstock to a pressure higher than the pressure in the reaction zone at the outlet of the conduit 28. Oxygen is suitably dissolved in the feedstock before said feedstock is injected into the reaction zone and preferably the feedstock is in at least substantially a saturated condition with respect to oxygen. Thus, when the feedstock enters the reaction zone 3 the drop in pressure will cause a certain quantity of the dissolved and/or dispersed oxygen to be liberated from the feedstock and to thereby provide oxygen in a free condition for the reaction zone. Saturation depends on the pressure and temperature and the feedstock would be supersaturated if the pressure or temperature changes sufficiently. Supersaturation could occur at the outlet of the conduit 28 and effect turbulence in the feedstock by liberation of oxygen.

Liquid atomizing means 30 are provided to atomize a fluid such as the ferment and/or additional feedstock and introduce same into the reaction zone in an atomized condition. The atomized liquid would have a large surface area per unit of weight and effect more intimate contact between same and the gas phase in the reaction zone 3. Any suitable atomizing means can be provided and, as shown, a plurality of atomizing nozzles 31 are mounted in the reaction zone 3 with the outlet openings thereof in communication with the reaction zone for the introduction of atomized liquid thereinto. A conduit 32 connects a pump 33 to a suitable source of liquid with the pump then being connected to the atomizing nozzles 31 by a conduit 34. The source of liquid can be from a separate source of feedstock and/or a lower portion of the reaction zone 3 for withdrawal of ferment to be atomized by the atomizing means 30. It is to be noted that certain of the atomizing nozzles 31 can be used to atomize fresh feedstock and certain of the remaining nozzles can be used to atomize ferment from the reaction zone 3.

The present invention is more fully understood by a description of the operation thereof. Feedstock is introduced into the reaction zone 3 and the reaction mixture is innoculated with a suitable microorganism. Circulation of the feedstock or ferment is effected by the turbine 14 and also by the atomizing means 30. Feedstock preferably is continually supplied to the reaction zone 3 by the pump 27 from the source 26 with the feedstock preferably being at least substantially saturated with oxygen. The rate of feed is determined by the growth rate of the microorganism and its rate of consumption of the feedstock. To further enhance the oxygen transfer rate, liquid, as described above, is atomized by the atomizing means 30. Most fermentation processes are of an exothermic nature and as such the heat exchange means 10 remove heat from the ferment to maintain an optimum growth temperature. Any type of heat exchange means 10 can be provided and as shown the heat exchange means is positioned in the throat of the draft tube 5 adjacent the top end 6 thereof whereby the turbine 14 provides circulation of the ferment past the heat exchange means. If the process if of a foam type, the foam breaker 21 is operable to separate the foam into a liquid phase and a gas phase. The product produced by the fermentation of the feedstock and culturing of the microorganism is withdrawn from the reaction zone through the conduit 20 whereby same is supplied to other suitable equipment for further processing of the product as is well known in the art. It is to be noted that although the atomizing nozzles 31 are positioned around the interior of the vessel 2 and directed generally radially inward, the atomizing nozzles can be positioned to spray downwardly or upwardly or at any angular position and preferably are adjustable so as to control the size of droplets produced by the atomization. Generally speaking, the larger the vessel 2 the larger the droplets that would be desired.

For example, in the production of single cell protein a feedstock containing methanol can be used with the feedstock further containing mineral nutrients and other elements necessary to the growth of the microorganism. Illustrative of microorganisms useful for processes such as this would be bacteria, such as *Pseudomonas methanica* or yeasts, such as *Hansenula polymorpha* wherein the operating temperature of the fermentation apparatus would be in the range of approximately 35°C to 45°C for rapid growth.

It is to be understood that while I have illustrated and described certain forms of my invention, it is not to be limited to the specific form or arrangement of parts herein described and shown.

What is claimed as desired to be secured by Letters Patent is:

1. A method of culturing a microorganism by fermentation of a carbon and energy source, said method comprising:
   a. at least substantially saturating and pressurizing a portion of a feedstock with an oxygen-containing gas;
   b. introducing said feedstock into a fermenting reaction zone containing a microorganism for fermenting said feedstock; said reaction zone being at a pressure lower than the pressure of said feedstock so that a gas phase is formed in said reaction zone;
   c. conducting fermentation in said reaction zone;
   d. atomizing a liquid selected from the group consisting of feedstock, ferment or mixtures thereof in said reation zone during fermentation so that said atomized liquid contacts with said gas phase in an upper portion of said reaction zone; and
   e. removing the product produced by the fermentation of the feedstock from said reaction zone.

2. The method as set forth in claim 1 wherein:
   a. said feedstock is supersaturated with an oxygen-containing gas.

3. The method as set forth in claim 1 including:
   a. circulating said feedstock in said reaction zone;
   b. removing heat from said reaction zone; and wherein
   c. said feedstock introduction, said atomizing and said product removal is substantially continuous.

4. The method as set forth in claim 3 wherein:
   a. said liquid includes feedstock.

5. The method as set forth in claim 4 wherein:
   a. said liquid includes ferment from said reaction zone.

6. The method as set forth in claim 4 wherein:
   a. said reaction zone is substantially foam filled with said foam being comprised of a ferment phase and an oxygen-containing gas phase; and including the step of
   b. breaking said foam into a ferment phase and a gas phase wherein said atomized liquid is contacted with the last mentioned gas phase.

* * * * *